United States Patent
Altiok

(10) Patent No.: US 10,627,413 B2
(45) Date of Patent: Apr. 21, 2020

(54) METHOD OF CANCER DIAGNOSIS, PROGRESSION AND RESPONSE TO THERAPY USING A PRIMARY XENOGRAFT MOUSE MODEL FOR CANCER SERUM BIOMARKER DISCOVERY

(71) Applicant: H. Lee Moffitt Cancer Center and Research Institute, Inc., Tampa, FL (US)

(72) Inventor: Soner Altiok, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 147 days.

(21) Appl. No.: 14/716,398

(22) Filed: May 19, 2015

(65) Prior Publication Data

US 2015/0253340 A1 Sep. 10, 2015

Related U.S. Application Data

(63) Continuation of application No. PCT/US2013/070778, filed on Nov. 19, 2013.

(60) Provisional application No. 61/727,870, filed on Nov. 19, 2012.

(51) Int. Cl.
  *G01N 33/68* (2006.01)
  *C12Q 1/6886* (2018.01)
  *G01N 33/574* (2006.01)
  *G01N 33/50* (2006.01)

(52) U.S. Cl.
  CPC ....... *G01N 33/6893* (2013.01); *C12Q 1/6886* (2013.01); *G01N 33/5088* (2013.01); *G01N 33/57484* (2013.01); *C12Q 2600/158* (2013.01); *G01N 2570/00* (2013.01); *G01N 2800/52* (2013.01); *G01N 2800/60* (2013.01)

(58) Field of Classification Search
  CPC ........... G01N 2800/52; G01N 33/5082; G01N 2800/60; A01K 2267/0331; A01K 67/0271; C12Q 1/6886; C12Q 2600/158
  See application file for complete search history.

(56) References Cited

PUBLICATIONS

He Y. et al. "LC-MS/MS Analysis of Ovarian Cancer Metastasis-Related Proteins Using a Nude Mouse Model: 14-3-3 Zeta as a Candidate Biomarker" Journal of Proteome Research 2010, 9, 6180-6190.*
Morton C.L. et al. Nature Protocols, vol. 2, No. 2 (2007), pp. 247-250.*
Kataoka H. et al. FEBS Journal 277 (2010) 2230-2237.*
Sun Z.-L. et al. Biochimica et Biophysica Acta 1774 (2007) 764-771.*
Waiker et al (J Am Soc Nephrol. Jan. 2012; 23(1):13-21) (Year: 2012).*
Brooks (Genome Res. Feb. 2012;22(2):183-7) (Year: 2012).*
Wei et al (Journal of Proteome Research 2011, 10, 161-174) (Year: 2011).*
International Search Report for PCT/US2013/070778, International filing date Nov. 19, 2013, dated Mar. 7, 2014.
International Preliminary Report on Patentability for PCT/US2013/070778, International filing date Nov. 19, 2013, dated May 28, 2015.
Cortez, et al., MicroRNA Identification in plasma and serum: a new tool to diagnose and monitor diseases. Expert Opinion on Biological Therapy, vol. 9, No. 6, pp. 703-711 (2009).
Fichtner, et la., Establishment of patient-derived non-small cell lung cancer xenografts as models for identification of predictive biomarkers. Clinical Cancer Research, vol. 14, No. 20, pp. 6456-6468 (2008).
Kulasingam et al., Strategies for discovering novel cancer biomarkers through utilization of emerging technologies. Nature Clinical Practice Oncology, vol. 5, No. 10, pp. 588-599 (2008).
Tang, et al., A xenograft mouse model coupled with in-depth plasma proteome analysis facilitates identification of novel serum biomarkers for human ovarian cancer. Journal of Proteome Research, vol. 11, No. 2, pp. 678-691 (2011).
Tentler, et al., Patient-derived tumour xenografts as models for oncology drug development. Nature Reviews Clinical Oncology, vol. 9, No. 6, pp. 338-350 (Jun. 2012).
Choi et al., Lessons from patient-derived xenografts for better in vitro modeling of human cancer. Advanced Drug Delivery Reviews. 2014. vol. 79-80: 222-237.
Siolas and Hannon. Patient Derived Tumor Xenografts: transforming clinical samples into mouse models. Cancer Res. 2013. vol. 73 (No. 17): 5315-5319.

* cited by examiner

*Primary Examiner* — Brian Gangle
*Assistant Examiner* — Andrea K McCollum
(74) *Attorney, Agent, or Firm* — Michele L. Lawson; Smith & Hopen, P.A.

(57) ABSTRACT

A method of determining disease diagnosis, progression and response to therapy through the use of xenograft animal models for determining cancer biomarkers is presented. In use, a tumor from a patient is transplanted into an animal model such as a mouse. Expression levels of biomarkers for a disease are assessed in the serum of the animal model. A personalized gene expression profile or biomarker gene signature may be obtained from the expression levels of the biomarkers which can be used to determine disease recurrence, progression and response to therapy.

5 Claims, 7 Drawing Sheets

METHOD OF CANCER DIAGNOSIS, PROGRESSION AND RESPONSE TO THERAPY USING A PRIMARY XENOGRAFT MOUSE MODEL FOR CANCER SERUM BIOMARKER DISCOVERY

CROSS REFERENCE TO RELATED APPLICATIONS

This application is a continuation of prior filed International Application, No. PCT/US2013/070778 filed on Nov. 19, 2013, which claims priority to U.S. Provisional Application No. 61/727,870, entitled "Primary Xenograft Mouse Model of Human Cancer as a Platform for Personalized Cancer Serum Biomarker Discovery", filed on Nov. 19, 2012, the entire contents of which are hereby incorporated by reference into this disclosure.

FIELD OF INVENTION

This invention relates to tumorigenic assays. Specifically, the invention provides a method of detecting tumor growth as well as monitoring tumor progression/regression and assessing the therapeutic response of the tumor to an agent using a biomarker signature derived from patient-derived mouse xenograft models.

BACKGROUND OF THE INVENTION

Early detection of cancer is generally recognized as the most effective strategy to reduce mortality. However, frequently cancer patients are diagnosed with advanced stage disease which adversely affects clinical outcome. Tumor-derived, circulating proteins can be potentially used as biomarkers for detection of cancer, for monitoring of disease progression, regression and recurrence, and for assessment of therapeutic response. If a test could be developed to detect cancer in its early stages, the lives of many patients might be extended. However, blood has numerous plasma proteins and identification of low abundance tumor-derived proteins is challenging.

SUMMARY OF INVENTION

The inventors have shown that patient tumor tissue that grows in immunocompromised mice allows identification of secreted tumor specific biomarkers, which may be used to develop non-invasive blood tests for individual cancer patients to detect tumor growth, regression and recurrence.

In an embodiment, a method of diagnosing cancer in a patient is presented. The method comprises removing tumor tissue from the patient; transplanting the tumor tissue in an animal model; obtaining the expression levels of at least one gene or gene expression product of the tumor by taking a sample of serum from the animal model; and establishing a biomarker gene signature for the patient based on the expression levels of the at least one gene or gene expression product of the tumor; wherein the expression levels indicate increased cancer risk.

A sample of serum or blood may be taken from the patient once the biomarker gene signature has been established to detect recurrence of the cancer in the patient. The animal model may be a mouse model. The expression levels of the at least one gene or gene expression product may by identified by sequencing using mass spectrometry.

In another embodiment, a method of monitoring the progression of cancer in a patient is presented. The method is comprised of removing tumor tissue from the patient; transplanting the tumor tissue in an animal model; sampling serum of the animal model to obtain an expression level of at least one gene or gene expression product from the tumor tissue and establishing a biomarker gene signature for the patient based on the expression level of the at least one gene or gene expression product of the tumor.

After establishing a biomarker gene signature or expression profile based on the xenograft tumor, serum or blood from the patient is sampled at a first timepoint to obtain a first expression level of at least one gene or gene expression product based on the biomarker gene signature and at a second timepoint to obtain a second expression level of the at least one gene or gene expression product based on the biomarker gene signature wherein the second timepoint is at a time period after the first timepoint and after the administration of the agent to the patient. The expression levels of the at least one gene or gene expression product taken from the patient at the first time point are then compared to the expression levels of the at least one gene or gene expression product taken from the patient at the second timepoint and increased expression levels at the second timepoint as compared to the first timepoint indicate disease progression.

In a further embodiment, a method of predicting the response of a patient to therapy for a neoplasia is presented comprising: removing tumor tissue from the patient; transplanting the tumor tissue in an animal model; sampling serum of the animal model to obtain an expression level of at least one gene or gene expression product from the tumor tissue; and establishing a biomarker gene signature for the patient based on the expression level of the at least one gene or gene expression product of the tumor.

After establishing a biomarker gene signature or expression profile based on the xenograft tumor, serum or blood from the patient is sampled at a first timepoint to obtain a first expression level of at least one gene or gene expression product based on the biomarker gene signature. An agent thought to treat the neoplasia is then administered to the patient. Serum from the patient is taken at a second timepoint to obtain a second expression level of the at least one gene or gene expression product based on the biomarker gene signature with the second timepoint being at a time period after the first timepoint and after the administration of the agent to the patient. The first and second expression levels taken from the patient are then compared and a therapeutic response is determined based on the comparison.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
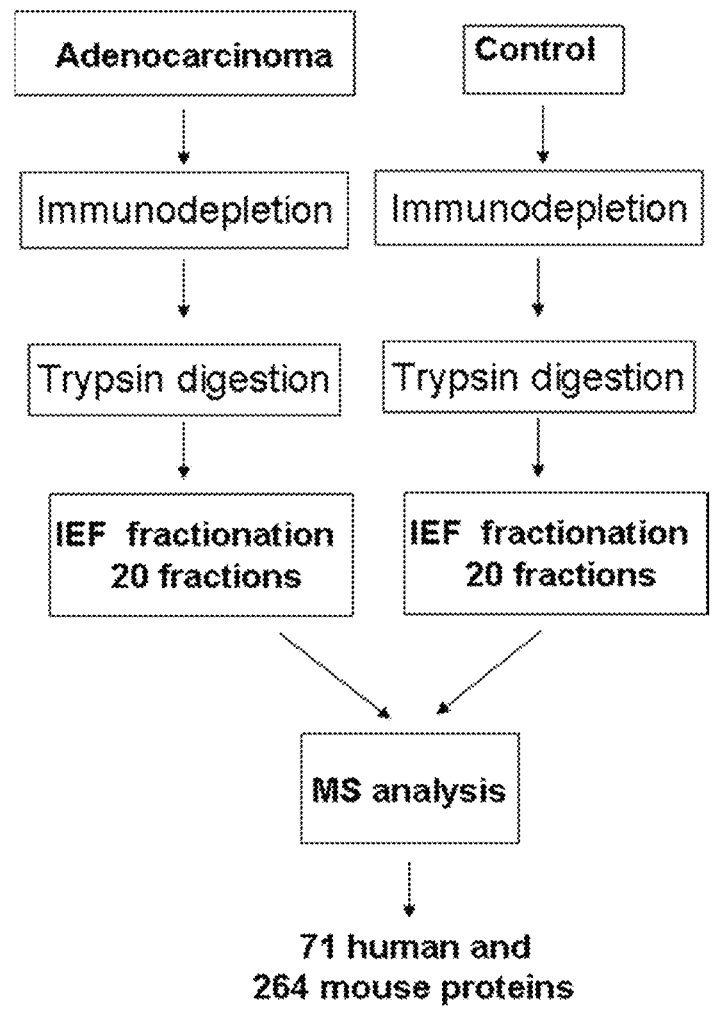
FIG. 1 is a flowchart illustrating an overview of the process used for identification of human tumor proteins in patient-derived mouse xenograft models.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the tenth of the unit. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described. It is to be understood, even if it is not always explicitly stated that all numerical designations are preceded by the term "about".

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

As used in the specification and claims, the singular form "a", "an" and "the" include plural references unless the context clearly dictates otherwise.

The term "agent" as used herein describes a composition, compound, chemical or extract that can be administered or tested by the present invention as a modulator of a given gene. The chemical can be of any composition such as inorganic, organic, or a biomolecule. A biomolecule can be a molecule of any biological origin that can be found in or produced by, at least in part, a cell. This definition includes, but is not limited to, polypeptides, lipids, nucleic acids, carbohydrates and combinations thereof "Agent" is used interchangeably herein with "compound", "composition", "chemical", "drug", and "extract".

"Patient" is used to describe an animal, preferably a human, to whom treatment is administered, including prophylactic treatment with the compositions of the present invention. "Subject" and "patient" are used interchangeably herein.

The genes of the present invention may serve as biomarkers for: (1) the diagnosis of disease; (2) the prognosis of diseases (e.g. monitoring disease progression or regression from one biological state to another); (3) the susceptibility or prediction of response to treatment for a disease; or (4) the evaluation of the efficacy to a treatment for disease. For the diagnosis of disease, the level of the specific gene in the subject can be compared to a baseline or control level in which if the level is above the control level, a certain disease is implicated. The prognosis of disease can be assessed by comparing the level of the specific gene biomarker at a first timepoint to the level of the biomarker at a second timepoint which occurs at a given interval after the first timepoint. The prediction of response to treatment for a disease can be determined by obtaining the level of a specific gene biomarker and correlating this level to an overall senescence score. The evaluation of the efficacy of the treatment for a disease can be assessed by comparing the level of the specific gene biomarker at a first timepoint before administration of the treatment to the level of the biomarker at a second timepoint which occurs at a specified interval after the administration of the treatment.

The term "expression level" as used herein refers to detecting the amount or level of expression of a biomarker of the present invention. The act of actually detecting the expression level of a biomarker refers to the act of actively determining whether a biomarker is expressed in a sample or not. This act can include determining whether the biomarker expression is upregulated, downregulated or substantially unchanged as compared to a control level expressed in a sample. The expression level in some cases may refer to detecting transcription of the gene encoding a biomarker protein and/or to detecting translation of the biomarker protein.

Expression of genes/transcripts and/or polypeptides encoded by the genes represented by the biomarkers of the present invention can be measured by any of a variety of methods known in the art. In general, expression of a nucleic acid molecule (e.g. RNA or DNA) can be detected by any suitable method or technique of measuring or detecting gene or polynucleotide sequence or expression. Such methods include, but are not limited to, polymerase chain reaction (PCR), reverse transcriptase PCR (RT-PCR), in situ PCR, quantitative PCR (q-PCR), in situ hybridization, Southern blot, Northern blot, sequence analysis, microarray analysis, detection of a reporter gene, or any other DNA/RNA hybridization platforms.

The term "quantifying" or "quantitating" when used in the context of quantifying transcription levels of a gene can refer to absolute or relative quantification. Absolute quantification can be achieved by including known concentration(s) of one or more target nucleic acids and referencing the hybridization intensity of unknowns with the known target nucleic acids (e.g. through the generation of a standard curve). Alternatively, relative quantification can be achieved by comparison of hybridization signals between two or more genes, or between two or more treatments to quantify the changes in hybridization intensity and, by implication transcription level.

Methods to measure protein/polypeptide expression levels of selected biomarkers in the present invention include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF), mass spectrometry, microcytometry, microarray, microscopy, fluorescence activated cell sorting (FACS), flow cytometry, and assays based on a property of the protein including but not limited to DNA binding, ligand binding, or interaction with other protein partners. In some embodiments, mass spectrometry is used to sequence the biomarkers.

The terms "diagnosing" or "diagnosis" as used herein refers to the determination of whether a subject comprises a disease or condition such as cancer. "Diagnosing" can also refer to distinguishing one cancer from another.

The term "prognosis" refers to the determination or prediction of the course of disease or condition or to monitoring disease progression or regression from one biological state to another. Prognosis can include the determination of the time course of a disease, with or without treatment. Where treatment is included, the prognosis includes determining the efficacy of the treatment for the disease or condition.

The terms "risk or susceptibility" as used herein refers to the determination as to whether a subject would or would not respond to a particular therapy such as chemotherapy, such as one or more alkylating agents; radiotherapy; adjuvant therapy; surgery; or a combination thereof in order to optimize therapy for an individual subject. Cancers that express biomarkers that are indicative of a more highly aggressive cancer or poor prognosis may be treated with more aggressive therapies.

The term "treatment" or "treating" or "therapy" as used herein refers to the ability to ameliorate, suppress, mitigate, or eliminate the clinical symptoms after the onset of a disease state. Treatment can include chemicals, such as chemotherapeutic agents or test compounds, and/or non-chemical treatment such as radiation, electrical pulses, and magnetic fields. An effective or successful treatment provides a clinically observable improvement.

The term "biomarker" is used herein to refer to a molecule whose level of nucleic acid or protein product has a quantitatively differential concentration or level with respect to an aspect of a biological state of a subject. "Biomarker" is used interchangeably with "marker" herein. The level of the biomarker can be measured at both the nucleic acid level as well as the polypeptide level. At the nucleic acid level, a nucleic acid gene or a transcript which is transcribed from any part of the subject's chromosomal and extrachromosomal genome, including for example the mitochondrial genome, may be measured. Preferably an RNA transcript, more preferably an RNA transcript includes a primary transcript, a spliced transcript, an alternatively spliced transcript, or an mRNA of the biomarker is measured. At the polypeptide level, a pre-propeptide, a propeptide, a mature peptide or a secreted peptide of the biomarker may be measured. A biomarker can be used either solely or in conjunction with one or more other identified biomarkers so as to allow correlation to the biological state of interest as defined herein. Specific examples of biomarkers covered by the present invention include genes involved in cell cycle regulation, apoptosis, cell proliferation, and angiogenesis. More specifically, biomarkers of the present invention include any known biomarkers of any cancers including those related to adenocarcinoma such as those listed in FIG. 2.

The term "biological state" as used herein refers to the result of the occurrence of a series of biological processes. As the biological processes change relative to each other, the biological state also changes. One measurement of a biological state is the level of activity of biological variables such as biomarkers, parameters, and/or processes at a specified time or under specified experimental or environmental conditions. A biological state can include, for example, the state of an individual cell, a tissue, an organ, and/or a multicellular organism. A biological state can be measured in samples taken from a normal subject or a diseased subject thus measuring the biological state at different time intervals may indicate the progression of a disease in a subject. The biological state may include a state that is indicative of disease (e.g. diagnosis); a state that is indicative of the progression or regression of the disease (e.g. prognosis); a state that is indicative of the susceptibility (risk) of a subject to therapy for the disease; and a state that is indicative of the efficacy of a treatment of the disease.

The term "cell" or "cells" is used synonymously herein and refers to in vitro cultures of mammalian cells grown and maintained as known in the art, as well as biological samples obtained from tumor specimens or normal specimens in vivo.

The term "sample" as used herein refers to any physical sample that includes a cell or a cell extract from a cell, a tissue, or an organ including a biopsy sample. The sample can be from a biological source such as a subject or animal, or a portion thereof, or can be from a cell culture. Samples from a biological source can be from a normal or an abnormal organism, such as an organism known to be suffering from a condition or a disease state such as a neoplasm, or any portion thereof. Samples can also be from any fluid, tissue or organ including normal and abnormal (diseased or neoplastic) fluid, tissue or organ. Samples from a subject or animal can be used in the present invention as obtained by the subject or animal and processed or cultured such that cells from the sample can be sustained in vitro as a primary or continuous cell culture or cell line. A "tumor sample" is a sample that includes at least one cell derived from at least one tumor.

A "therapeutically effective amount" as used herein is defined as concentrations or amounts of components which are sufficient to effect beneficial or desired clinical results, including, but not limited to, inhibiting neoplastic transformation of cells; inhibiting inappropriate cell growth; inhibiting the proliferation of neoplastic/cancerous cells; inducing apoptosis in neoplastic/cancerous cells; decreasing the level of a given biomarker in a sample; and enhancing the therapeutic effect of chemotherapy medications. Compositions of the present invention can be used to effect a favorable change in the condition whether that change is an improvement or a complete elimination of symptoms due to neoplasia/cancer. In accordance with the present invention, a suitable single dose size is a dose that is capable of preventing or alleviating (reducing or eliminating) a symptom in a subject when administered one or more times over a suitable time period. One of skill in the art can readily determine appropriate single dose sizes for systemic administration based on the size of the animal and the route of administration. The therapeutically effective amount of the compositions of the present invention encompasses providing cancer treatment or enhancing cancer treatment without causing significant side effects or adverse reactions.

The term "baseline level" or "control level" of biomarker expression or activity refers to the level against which biomarker expression in the test sample can be compared. In some embodiments, the baseline level can be a normal level, meaning the level in a sample from a normal patient. This allows a determination based on the baseline level of biomarker expression or biological activity, whether a sample to be evaluated for disease cell growth has a measurable increase, decrease, or substantially no change in biomarker expression as compared to the baseline level. The term "negative control" used in reference to a baseline level of biomarker expression generally refers to a baseline level established in a sample from the subject or from a population of individuals which is believed to be normal (e.g. non-tumorous, not undergoing neoplastic transformation, not exhibiting inappropriate cell growth). In other embodiments, the baseline level can be indicative of a positive diagnosis of disease (e.g. positive control). The term "positive control" as used herein refers to a level of biomarker expression or biological activity established in a sample from a subject, from another individual, or from a population of individuals, where the sample was believed, based on data from that sample, to have the disease (e.g. tumorous, cancerous, exhibiting inappropriate cell growth). In other embodiments, the baseline level can be established from a previous sample from the subject being tested, so that the disease progression or regression of the subject can be monitored over time and/or the efficacy of treatment can be evaluated.

The term "neoplasia", "cancer", "tumor", "cancerous", and malignant" as used herein, refer to the physiological condition in mammals that is typically characterized by unregulated cell growth or the presence of tumors. Any cancer that can be recognized using biomarkers may be benefited by this invention. Examples of cancers benefited by the present invention include, but are not limited to, myelomas; leukemias; lymphomas; sarcomas; carcinomas; myelodysplastic syndrome; brain cancer; cancer of the nervous system including gliomas, meningioma, medulloblastoma, schwannoma, and epidymoma; lung cancer including non-small cell lung cancer and small cell lung cancer; breast cancer; prostate cancer; testicular cancer; bladder cancer; bone marrow cancer; cervical cancer; chronic lymphocytic leukemia; colorectal cancer; esophageal cancer; hepatocellular cancer; lymphoblastic leukemia; follicular lymphoma; lymphoid malignancies of T or B cell origin; melanoma and other skin cancers; myelogenous leukemia; myeloma; oral cancer; ovarian cancer; spleen cancer; pancreatic cancer; stomach cancer; colorectal cancer; renal cell carcinoma; and head and neck carcinoma.

The term "gene expression product" or "expression product" as used herein refers to an RNA transcribed from a gene (either pre- or post-processing) or an amino acid (e.g. a polypeptide, protein, or peptide regardless of any secondary modifications, such as glycosylation, lipidation or phosphorylation) encoded by the gene and generated by the gene when the gene is transcribed (either pre- or post-modification) and translated. An agent is said to increase gene expression if the application of a therapeutically effective amount of the agent to a cell or subject results in an increase in either an RNA or polypeptide expression product or both. An agent is said to decrease gene expression if the application of a therapeutically effective amount of the agent to a cell or subject results in a decrease in either an RNA or polypeptide expression product or both.

The term "polynucleotide" as used herein refers to a polymeric molecule that has a backbone that supports bases capable of hydrogen bonding to typical polynucleotides. The polymer backbone presents the bases in a manner that is effective to allow such hydrogen bonding in a sequence specific fashion between the polymeric molecule and a typical polynucleotide, such as single-stranded DNA. Polymeric molecules include both single and double stranded DNA or RNA and can include polymers having backbone modifications. It includes the recited sequences as well as their complementary sequences, which can be easily ascertained by those of ordinary skill in the art.

The term "nucleic acid" as used herein may be double-stranded, single-stranded, or contain portions of both double and single stranded sequence. If the nucleic acid is single-stranded, the sequence of the other strand is also identifiable and thus the definition includes the complement of the sequence disclosed.

The term "polypeptide" as used herein refers to a compound made up of a single-chain of amino acid residues that are linked by peptide bonds. The term "protein" may be synonymous with the term "polypeptide" or may refer, in addition, to a complex of two or more polypeptides. Generally, polypeptides and proteins are formed predominantly of naturally occurring amino acids.

An "isolated polynucleotide" as used herein refers to a polynucleotide which is separated from other nucleic acid molecules which are present in the natural source of the polynucleotide. Preferably, an "isolated polynucleotide" is free of sequences which naturally flank the polynucleotide in the genomic DNA of the organism from which the nucleic acid is derived. An "isolated polynucleotide" is substantially free of other cellular material, gel materials, and culture medium when produced by recombinant techniques, or substantially free of chemical precursors or other chemicals when chemically synthesized. The polynucleotides of the present invention may be isolated from a variety of sources, such as PCR amplification from genomic DNA, mRNA, or cDNA libraries derived from the mRNA using standard techniques.

The term "differential expression" as used herein refers to qualitative or quantitative differences in the temporal and/or spatial gene expression patterns within and among cells and tissues. A differentially expressed gene may qualitatively have its expression altered, including an activation or inactivation, such as in normal versus diseased tissue. Genes may be turned off or on in a given state relative to another state thus allowing comparison of two or more states. A qualitatively regulated gene may exhibit an expression pattern within a state or cell type that can be detectable by standard techniques. Alternatively, the difference in expression may be quantitative such that expression of the gene is modulated, up-regulated (resulting in an increased amount of transcript), or down-regulated (resulting in a decreased amount of transcript). The degree to which expression varies needs to be large enough to quantify via standard characterization techniques such as expression arrays, quantitative reverse transcriptase PCR, Northern blot analysis, real-time PCR, in situ hybridization, and RNase protection.

The term "expression profile" as used herein refers to a genomic expression profile, for example an expression profile of microRNAs. The profiles may be generated by any means for determining a level of a nucleic acid sequence, e.g. quantitative hybridization of microRNA, labeled micro- RNA, amplified microRNA, cDNA, quantitative PCR, ELISA for quantitation, etc. The profile must allow for the analysis of differential gene expression between two samples.

The terms "overexpression" and "underexpression" as used herein refers to the expression of a gene of a patient at a greater or lesser level, respectively, than the normal or control expression of the gene, as measured by gene expression product expression such as mRNA or protein expression, in a sample that is greater than the standard of error of the assay used to assess the expression. A "significant" expression level may be a level which either meets or is above or below a predetermined score for a gene.

The terms "favorable outcome" or "favorable prognosis" as used herein refers to long time to progression, long term survival, and/or good response. Conversely, an "unfavorable outcome" or "unfavorable prognosis" refers to short time to progression, short term survival, and/or poor response.

The terms "long term survival" and "short term survival" as used herein refer to the length of time after receiving a first dose of a treatment that a cancer patient is predicted to live. A "long term survivor" refers to a patient expected to have a slower rate of progression or later death from the tumor than those patients identified as short term survivors. "Enhanced survival" or a "slow rate of death" refer to estimated life span determinations that are based on a characteristic such as the size, sequence, composition, activity or amount of a given biomarker as compared to a reference standard in which 60% or more of the population will be alive a sufficient time period after receiving the first dose of treatment. "Faster rate of death" or "diminished survival" refer to estimated life span determinations that are based on a characteristic such as the size, sequence, composition, activity or amount of a given biomarker as compared to a reference standard in which less than 50% of the population will not live a sufficient time period after receiving the first dose of treatment. In some embodiments, the "sufficient time period" may be at least 6, 12, 18, 24, 30 or 36 months or more measured from the first day of receiving cancer therapy.

A cancer is "responsive" to a therapeutic agent or there is a "good response" to a treatment if its rate of growth is inhibited as a result of contact with the therapeutic agent, compared to its growth in the absence of contact with the therapeutic agent. Growth of a cancer can be measured in a variety of ways, for instance, the characteristic, e.g., size of a tumor or the expression of tumor markers appropriate for that tumor type may be measured.

A cancer is "non-responsive" or has a "poor response" to a therapeutic agent or there is a poor response to a treatment if its rate of growth is not inhibited, or inhibited to a very low degree, as a result of contact with the therapeutic agent when compared to its growth in the absence of contact with the therapeutic agent. As stated above, growth of a cancer can be measured in a variety of ways, for instance, the size of a tumor or the expression of tumor markers appropriate for that tumor type may be measured.

A "gene expression signature" or a "biomarker gene signature" as used herein refers to a specific pattern of gene modulation of a given gene in neoplasias. The biomarker gene signature obtained by the methods disclosed herein are personalized to the patient whose tumor is used in the xenograft. The biomarker gene signature can be used by the clinician to determine the best course of treatment for the patient including diagnosis/recurrence, progression of disease, and response to therapy/treatment.

The current invention refers to a method for identifying tumor-secreted proteins as biomarkers in mice and then monitoring the biomarkers in human patients for cancer detection, progression and response to therapy. The basic method for identifying the biomarkers involves implanting a patient tumor sample into a mouse xenograft model, where it will secrete growth factors, cytokines, and other proteins into the blood of the mouse as it grows. Samples of mouse serum are then collected and the proteins specific to the human tumor are identified by sequencing using mass spectrometry. Changes in the biomarkers can be identified that correlate with drug response or that correlate with tumor progression.

Specifically, this invention involves utilization of xenograft mouse models bearing fresh human cancer tissue or cells as a source to discover cancer specific protein/peptide serum biomarker signatures for individual patients. The inventors demonstrated that plasma/serum obtained from xenograft models of human cancer can be used to identify low-abundance cancer specific biomarkers by mass spectrometry. The data revealed that tumor proteins/peptides are relatively enriched in mouse blood to allow detection of proteins/peptides that are difficult to identify in patients' blood due to masking and/or dilution. Identification of protein/peptide signatures of individual patient's tumor in xenograft mice may allow for the development of individualized blood tests to monitor cancer growth, recurrence and therapy response. In addition, identification of the protein/peptide signatures can allow for a better understanding of the biological behavior of individual tumors to develop more efficient drug treatments.

Example

An overview of the experimental workflow is shown in FIG. 1. Mouse serum was immunodepleted of the 7 most abundant proteins using a Seppro® Mouse Spin Columns and concentrated to 300 µL using 5 kDa MWCO spin concentrators. Denaturing buffer was added and buffer exchange step was repeated twice. After digestion with porcine trypsin the samples were de-salted followed by elution process. Peptide solutions were IEF fractionated to 20 fractions. The peptides are extracted and dried. After re-suspension the samples were injected on column for MS analysis. A nanoflow liquid chromatograph (U3000, Dionex, Sunnyvale, Calif.) coupled to a quadrupole time-of-flight mass spectrometer (QSTAR® Elite, Applied Biosystems, Foster City, Calif.) was used for tandem mass spectrometry peptide sequencing experiments.

Figure 2:
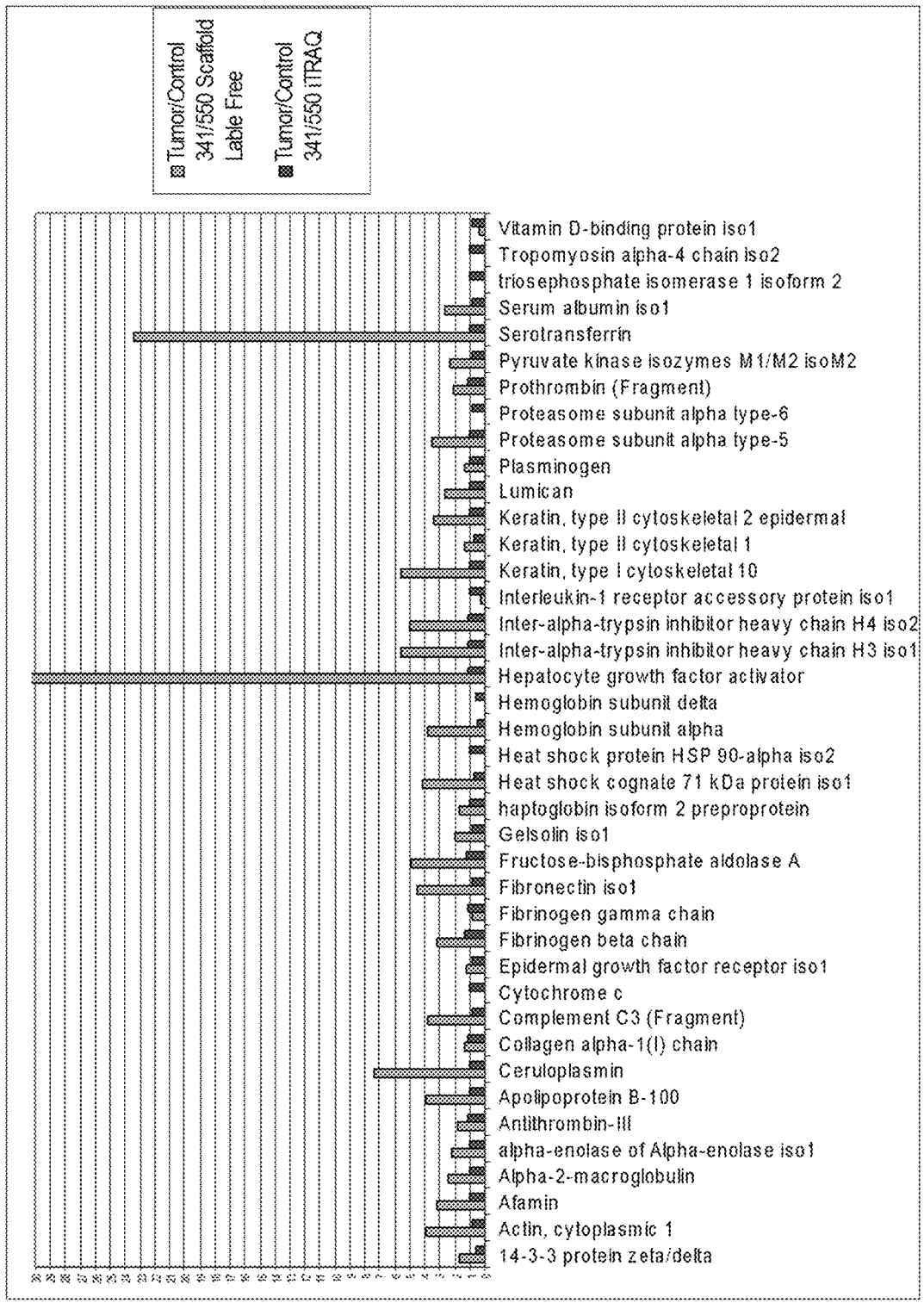
FIG. 2 is a graph depicting the identification of human tumor proteins in patient-derived mouse xenograft models.

FIG. 2 is a graph illustrating that plasma/serum obtained from xenograft models of human cancer prepared with fresh human tumor can be used to identify low-abundance cancer specific biomarkers by mass spectrometry. Serum/plasma profiling of patient derived xenograft models allows detection of cancer specific proteins that can be used to develop individualized cancer biomarker profiles for cancer patients to monitor therapeutic response and disease recurrence. This approach may also allow development of therapeutic applications targeting the specific proteomic characteristics of each patient's tumor.

Many proteins such as β2M, Cep57-related protein, alpha-enolase, talin1, afamin, and HGFAi, which were isolated in the serum of this xenograft mouse model prepared from fresh tumor tissue of a lung cancer patient have been reported to be overexpressed in cancer cells and can be used as cancer specific biomarkers. Thus the approach described here can be utilized for cancer specific biomarker discovery and validation.

Figure 3A:
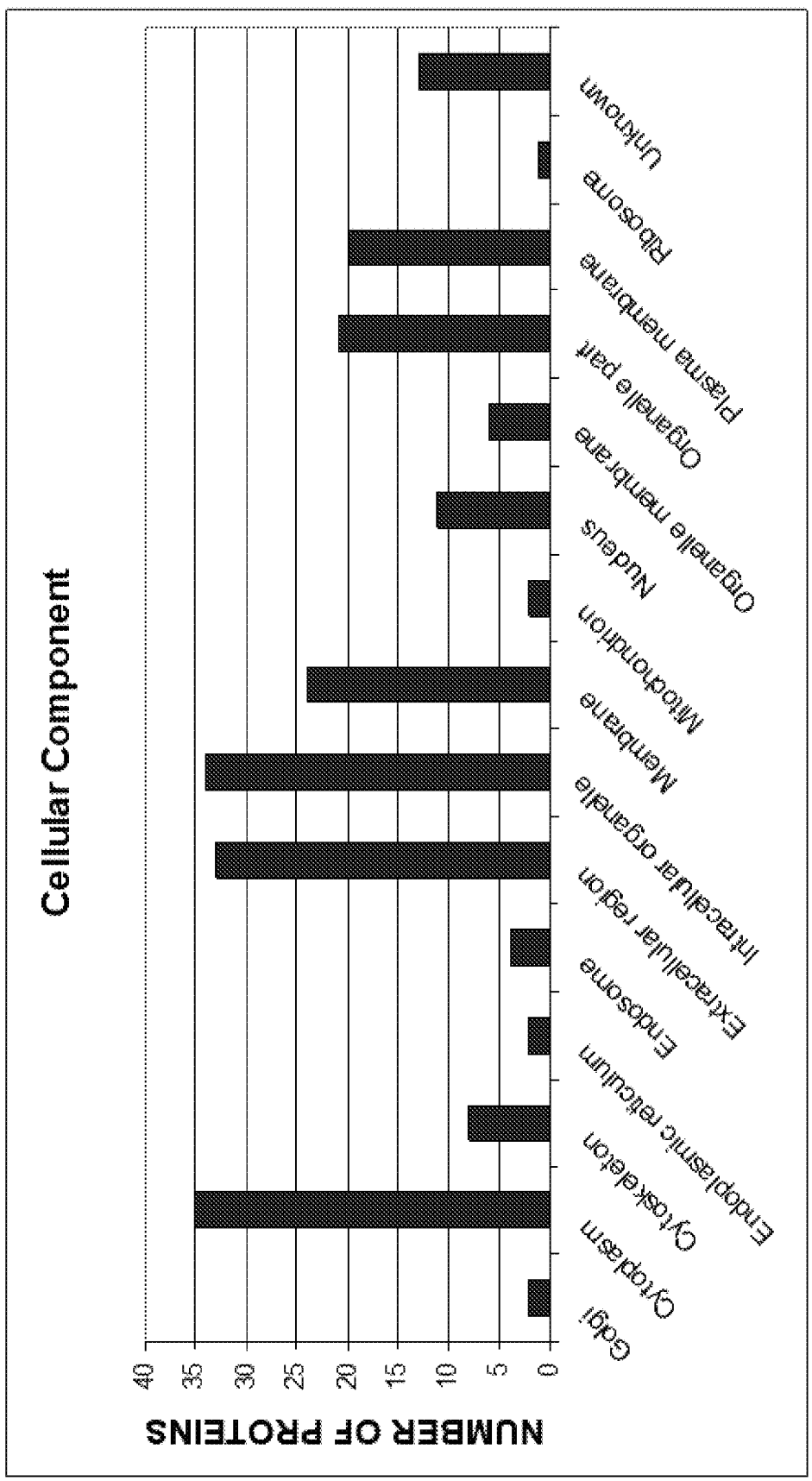
FIGS. 3A and 3B are a series of images depicting the cellular distribution of the detected proteins.
Figure 3B:
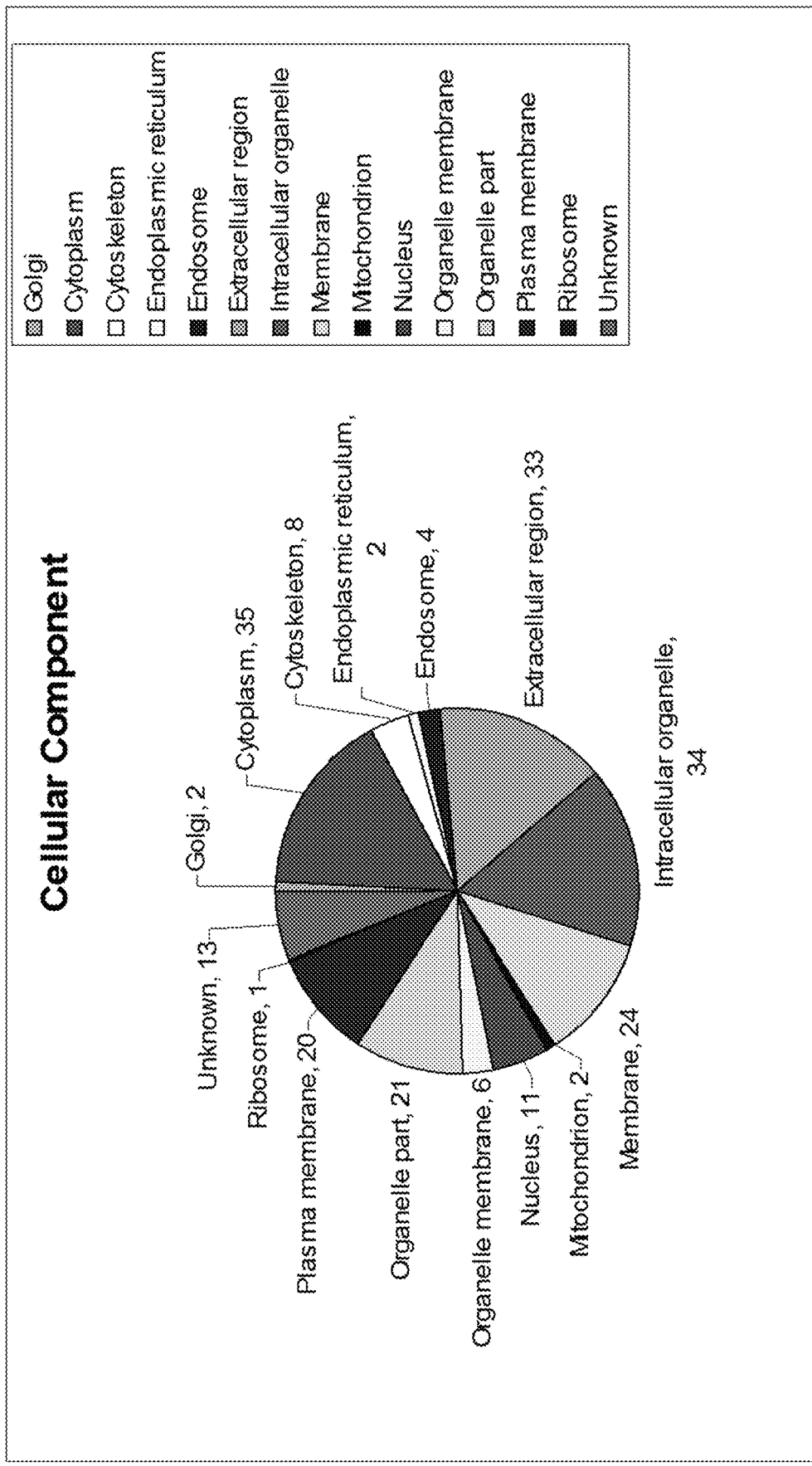

FIG. 3 illustrates the cellular distribution of the detected proteins. After using adenocarcinoma in a xenograft mouse and immunodepleting the mouse serum of the seven most abundant proteins, the inventors identified 71 human proteins and 264 mouse proteins with the average protein ratio for Tumor/Control being 2.6 for human and 1.15 for mice. Most of the human proteins appear to be up-regulated. (46 proteins out of 71 have a Tumor/Control ratio greater than 2.) For mouse proteins 28 proteins out of 264 have a Tumor/Control ratio greater than 2 and the rest appear to be unchanged. Among the isolated proteins, 15% are extracellular or secreted proteins, 16% are cytoplasmic, 29% are organelle proteins, 20% are membrane-associated proteins and 6% are nuclear or mitochondrial proteins.

Figure 4A:
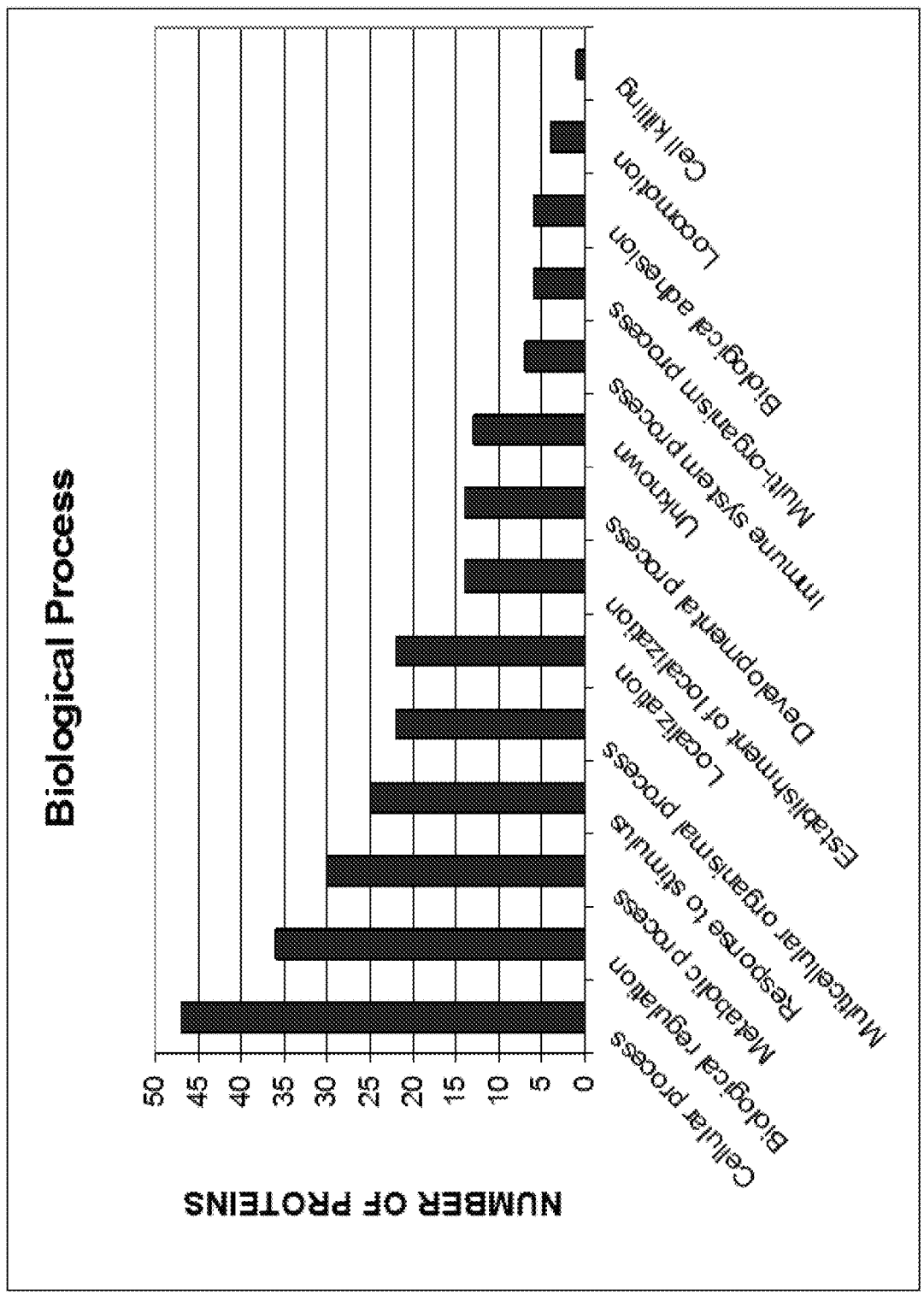
FIGS. 4A and 4B are a series of images depicting the biological activity of the detected proteins.
Figure 4B:
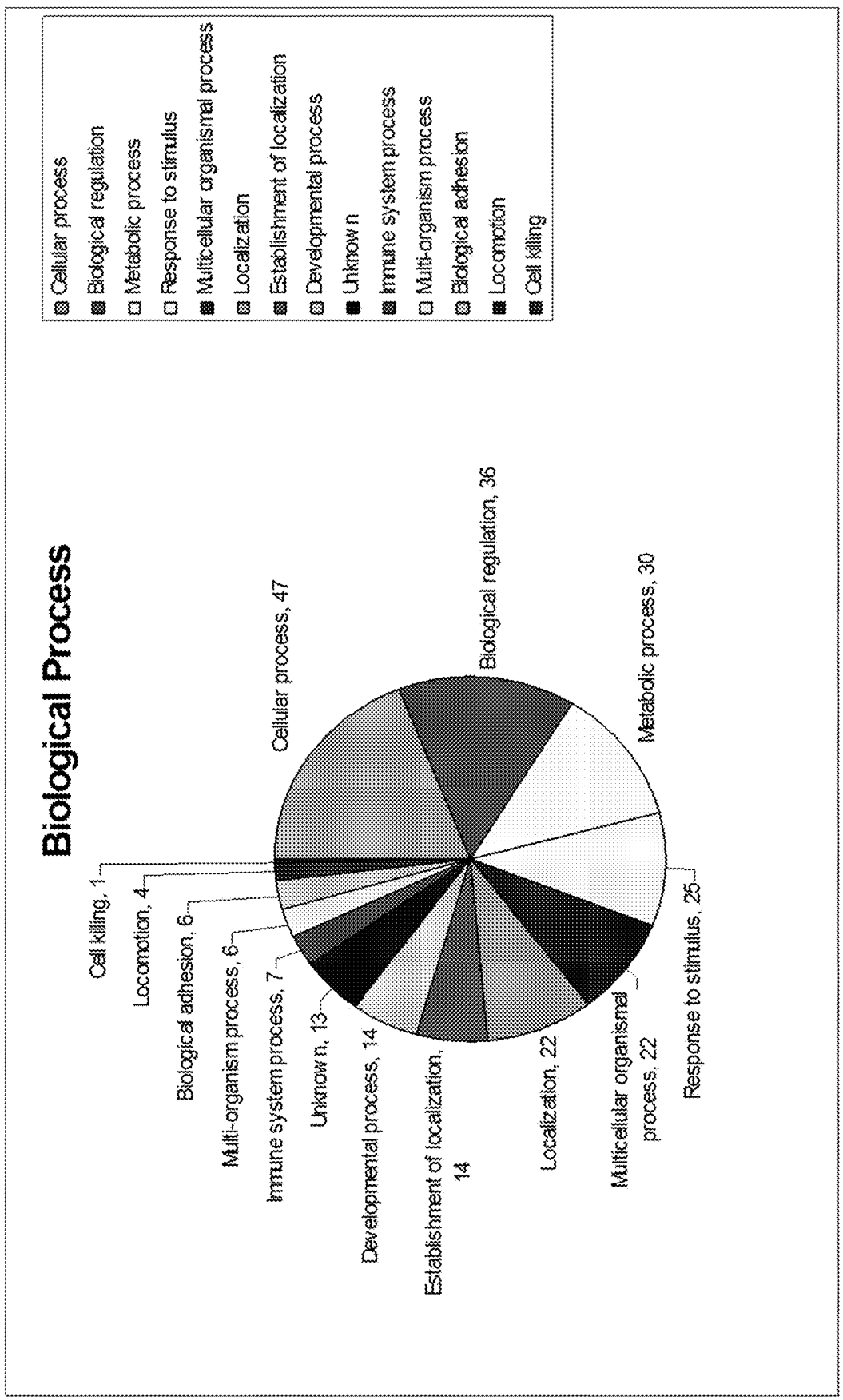

FIG. 4 illustrates the biological activity of the detected proteins. The analysis of proteomic data allows identification of the cellular functions of proteins detected in patient derived mouse serum samples.

Figure 5:
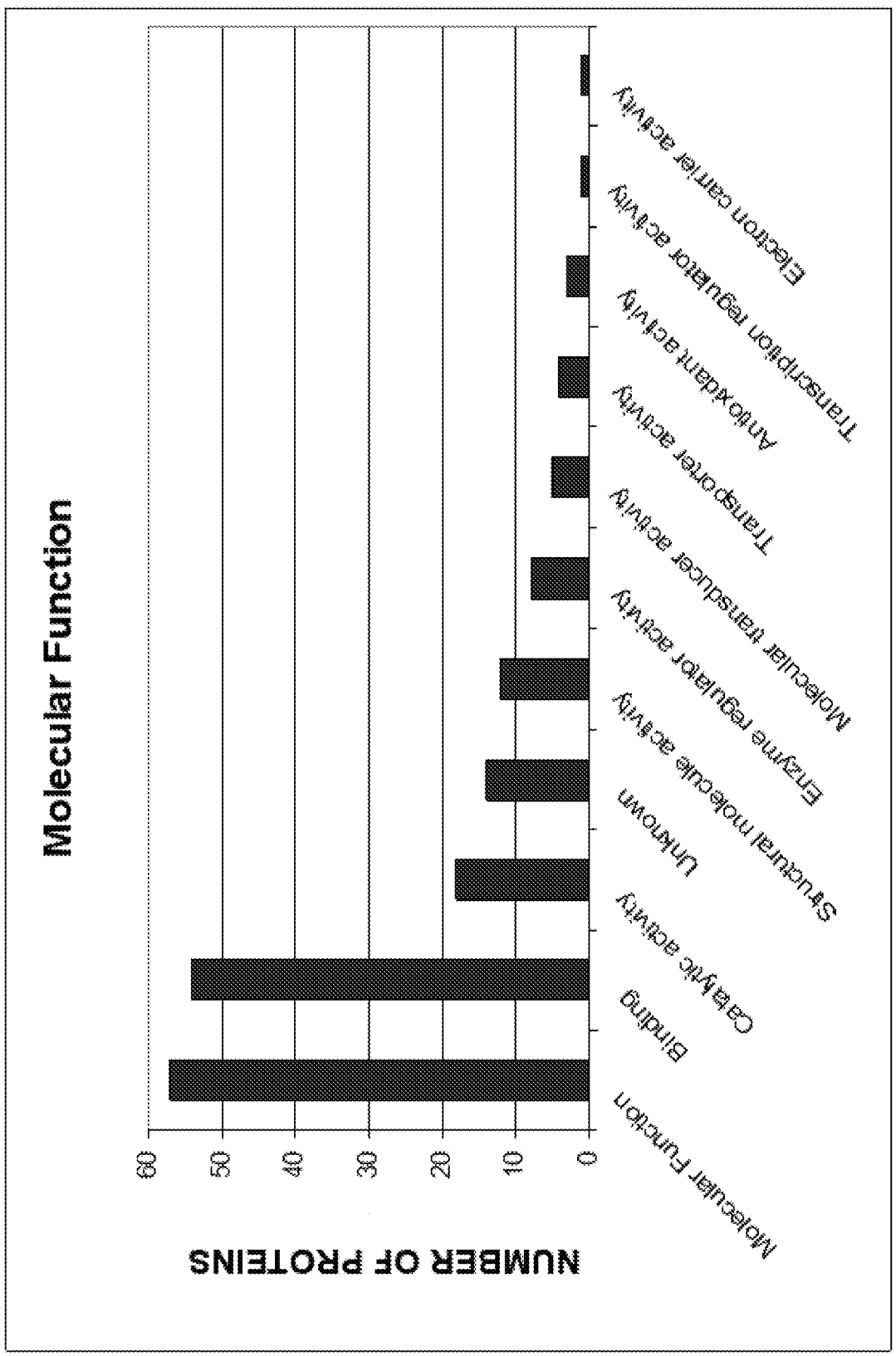
FIG. 5 is a graph illustrating the molecular functions of detected proteins.

FIG. 5 is a graph depicting the molecular functions of the detected proteins. The molecular function of the detected proteins can be determined by proteomic data analysis.

There are two main advantages of this method over searching for tumor-secreted biomarkers in the patient blood. First, putting a human tumor into a mouse allows the human tumor-secreted proteins to be seen against a background of mouse proteins in the mouse blood, where the human proteins can be easily distinguished from mouse proteins based on sequence alone. Second, the human proteins are greatly enriched when a 2 cm human tumor is put in a 20 gram mouse versus that same 2 cm tumor in a 200 lb human, where low-abundance proteins may be difficult to see against the numerous human plasma proteins.

Further, the new biomarkers found in the xenograft animal model can then be used to make personalized diagnosis and treatment decisions for the very patients whose tumors were analyzed in the mice. For example, personalized serum tumor biomarkers for individual cancer patients can be used to detect the early recurrence or metastasis of a given tumor in a specific patient. Alternatively, the biomarkers can be used to monitor tumor response to potential cancer therapies over time.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of diagnosing lung adenocarcinoma in a patient comprising:
    removing suspected adenocarcinoma tumor tissue from the lung of the patient;
    transplanting the suspected adenocarcinoma tumor tissue in an animal model;
    sampling serum from the animal model to obtain an expression level of proteins of the suspected adenocarcinoma tumor wherein the proteins are vitamin D-binding protein isoform 1; tropomyosin alpha-4 chain isoform 2; triosephosphate isomerase 1 isoform 2; serum albumin isoform 1; serotransferrin; pyruvate kinase isozyme M1/M2 isoform M2; prothrombin fragment; proteasome subunit alpha type-6; proteasome subunit alpha type-5; plasminogen; lumican; keratin, type II cytoskeletal 2 epidermal; keratin, type II cytoskeletal 1; keratin, type I cytoskeletal 10; interleukin-1 receptor accessory protein isoform 1; inter-alpha-trypsin inhibitor heavy chain H4 isoform 2; inter-alpha-trypsin inhibitor heavy chain H3 isoform 1; hepatocyte growth factor activator; hemoglobin subunit delta; hemoglobin subunit alpha; heat shock protein HSP 90-alpha isoform 2; heat shock cognate 71 kDa protein isoform 1; haptoglobin isoform 2 preproprotein; gelsolin isoform 1; fructose-bisphosphate aldolase A; fibronectin isoform 1; fibrinogen gamma chain; fibrinogen beta chain; epidermal growth factor receptor isoform 1; cytochrome c; complement C3 fragment; collagen alpha-1(I) chain; ceruloplasmin; apolipoprotein B-100; antithrombin-III; alpha enolase isoform 1; alpha-2 macroglobulin; afamin; and actin cytoplasmic 1;
    detecting the expression level of the proteins in the serum from the animal model using tandem mass spectrometry;
    sequencing the proteins detected in the serum from the animal model to differentiate human proteins from animal proteins;
    comparing the expression level of the proteins detected in the serum of the animal model and determined to be human proteins after sequencing to a control sample obtained from serum from a normal human subject to determine differential expression of the human proteins;
    wherein upregulated differential expression levels of the human proteins of the suspected adenocarcinoma tumor as compared to the expression levels of the human proteins from the normal subject diagnoses lung adenocarcinoma; and
    administering a drug for treating lung adenocarcinoma to the patient when a lung adenocarcinoma is diagnosed.

2. The method of claim 1, further comprising sampling serum from the patient to obtain an expression level of the proteins identified as being differentially expressed.

3. The method of claim 1, wherein the animal model is a rodent.

4. The method of claim 3, wherein the animal model is a mouse.

5. The method of claim 1, further comprising immunodepleting the serum in the animal model of the seven most abundant proteins after sampling the serum from the animal model.

* * * * *